United States Patent
Casu et al.

(10) Patent No.: US 11,345,127 B2
(45) Date of Patent: May 31, 2022

(54) SILICONE-GEL-COATED ADHESIVE LAYER STRUCTURE

(71) Applicant: BSN Medical GmbH, Hamburg (DE)

(72) Inventors: Sascha Casu, Hamburg (DE); Marco Peter Wogram, Oststeinbek (DE); Felix Krause-Kyora, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 485 days.

(21) Appl. No.: 15/574,609

(22) PCT Filed: May 13, 2016

(86) PCT No.: PCT/EP2016/060875
§ 371 (c)(1),
(2) Date: Nov. 16, 2017

(87) PCT Pub. No.: WO2016/184811
PCT Pub. Date: Nov. 24, 2016

(65) Prior Publication Data
US 2019/0344549 A1 Nov. 14, 2019

(30) Foreign Application Priority Data
May 18, 2015 (DE) .................. 10 2015 107 743.4

(51) Int. Cl.
| | |
|---|---|
| *B32B 27/12* | (2006.01) |
| *A61F 13/02* | (2006.01) |
| *A61L 15/22* | (2006.01) |
| *A61L 15/58* | (2006.01) |
| *B32B 5/02* | (2006.01) |
| *B32B 5/18* | (2006.01) |
| *B32B 7/12* | (2006.01) |
| *B32B 27/08* | (2006.01) |
| *B32B 27/26* | (2006.01) |
| *B32B 27/28* | (2006.01) |
| *B32B 27/30* | (2006.01) |
| *A61F 13/00* | (2006.01) |

(52) U.S. Cl.
CPC .......... *B32B 27/12* (2013.01); *A61F 13/0253* (2013.01); *A61L 15/22* (2013.01); *A61L 15/58* (2013.01); *B32B 5/022* (2013.01); *B32B 5/026* (2013.01); *B32B 5/18* (2013.01); *B32B 7/12* (2013.01); *B32B 27/08* (2013.01); *B32B 27/26* (2013.01); *B32B 27/28* (2013.01); *B32B 27/308* (2013.01); *A61F 2013/00702* (2013.01); *A61L 2300/608* (2013.01); *B32B 2250/02* (2013.01); *B32B 2255/02* (2013.01); *B32B 2255/102* (2013.01); *B32B 2262/02* (2013.01); *B32B 2262/14* (2013.01); *B32B 2307/718* (2013.01); *B32B 2405/00* (2013.01); *B32B 2535/00* (2013.01)

(58) Field of Classification Search
CPC ....... B32B 27/12; A61F 13/0253; A61L 15/22
See application file for complete search history.

(56) References Cited

U.S. PATENT DOCUMENTS

| | | |
|---|---|---|
| 2,878,142 A | 3/1959 | Bohaty |
| 4,838,253 A | 6/1989 | Brassington et al. |
| 6,284,328 B1 | 9/2001 | Leydecker et al. |
| 6,432,529 B1 * | 8/2002 | Harder ............... C09J 7/21 |
| | | 428/355 AC |
| 6,441,092 B1 | 8/2002 | Gielselman |
| 7,163,720 B1 | 1/2007 | Dhaler et al. |
| 2006/0154053 A1 | 7/2006 | Cain et al. |
| 2010/0267302 A1 | 10/2010 | Kantner et al. |
| 2013/0053748 A1 | 2/2013 | Cotton |
| 2014/0134375 A1 | 5/2014 | Guillo et al. |

FOREIGN PATENT DOCUMENTS

| | | |
|---|---|---|
| CN | 102803423 A | 11/2012 |
| EP | 0994169 A2 | 4/2000 |
| EP | 1194496 B1 | 11/2004 |
| JP | S51-29597 | 3/1976 |
| JP | 10118174 A | 5/1998 |
| JP | 4685301 B2 | 1/2003 |
| JP | 2003503540 A | 1/2003 |
| JP | 2004123991 A | 4/2004 |
| JP | 2012524159 A | 4/2010 |
| JP | 2015502988 A | 1/2015 |
| WO | 200078885 A1 | 12/2000 |
| WO | WO 2004/082935 A2 | 9/2004 |
| WO | 2010121033 | 10/2010 |
| WO | WO 2010/121033 A2 | 10/2010 |
| WO | WO 2011/022199 A2 | 2/2011 |
| WO | 2013062836 A1 | 5/2013 |

OTHER PUBLICATIONS

International Patent Application No. PCT/EP2016/060875 dated Jul. 29, 2016.
Xiaoling Liao, Wengfen Xu, Common Knowledge 1: Guidelines for Basic Experiments of Material Chemistry, Feb. 27, 2015, Metallurgical Industry Press.
Yixing Zhan, Changsha, Common Knowledge 2: Collection of Manufacture of Modern Chemical Small Commodities, Aug. 31, 1999, p. 286, Hunan University Press.

* cited by examiner

*Primary Examiner* — Chinessa T. Golden
(74) *Attorney, Agent, or Firm* — Shumaker, Loop & Kendrick, LLP

(57) ABSTRACT

The present invention relates to a silicone-gel-coated, adhesive layer structure, a method for the production thereof as well as the use thereof. The layer structure comprises a porous backing material, an intermediate layer applied to one side of the porous backing material and an adhesive layer made of a silicone gel applied to the intermediate layer.

23 Claims, No Drawings

SILICONE-GEL-COATED ADHESIVE LAYER STRUCTURE

The present invention relates to a silicone-gel-coated, adhesive layer structure, a method for the production thereof as well as the use thereof.

BACKGROUND OF THE INVENTION

Silicone-coated, adhesive structures display a range of innovative properties which make them of particular interest for medical uses. Thus, a silicone-based adhesive agent (called silicone gel in the following) is gentler and more pleasant for the skin than conventional acrylate adhesives. Silicone gels can, for example, be removed easily and with minimal detachment of skin cells and hair, and at the same time provide an optimal and constant adhesive force over the entire duration of the application. Repeated use is likewise possible without difficulty. In addition, silicone gels display a very good adhesion to other components present in the structure, for example to an acrylic acid copolymer. A transfer onto the skin can thereby be reduced or even prevented entirely, whereby additional cleaning steps to remove adhesive agent residues from the patient's skin can be dispensed with. These properties make adhesive structures coated with silicone gel of great interest for use in medicine, above all for use on patients with sensitive and fragile skin.

In order to guarantee an optimal wearing comfort, the backing materials of adhesive structures used in medicine are usually manufactured from a soft and elastic material. In order to supply oxygen or moisture as well as possible to the patient's skin lying under the adhesive structure, porous backing materials are particularly advantageous, as they allow transport of oxygen and/or moisture to the patient's skin lying under the adhesive layer structure. However, the porosity of the backing material often leads to problems in the production of adhesive structures based on silicone gel. Before they are crosslinked, silicone gels are flowable compounds which, when coated directly onto a porous backing, permeate it and often even re-emerge on the opposite side, which is called bleeding through. This would lead to a coated structure which has a degree of stickiness on both sides, which is undesired as a rule.

Silicone-coated, adhesive structures are known, for example, from US 2006/0154053 A1, in which porous backings (stockings) are disclosed which have an adhesive layer made of a silicone or acrylate. Between the porous backing (the stocking) and the adhesive layer made of silicone or acrylate, there is additionally an intermediate layer made of a silicone elastomer.

Silicone-coated, porous backings are likewise known from US 2010/0267302 A1.

Furthermore, silicone-coated substrates which have an intermediate layer are known from US 2007/0128263 A1. The material and shape of the substrates are unknown, however.

DESCRIPTION OF THE INVENTION

The object of the present invention is to provide an adhesive layer structure which comprises a porous backing material and an adhesive layer made of a silicone gel on only one side of the porous backing material, wherein the silicone gel is to be prevented from permeating or bleeding through the porous backing material. In addition, a good bonding of the adhesive silicone gel layer to the layer structure is to be guaranteed, in order to reduce or ideally entirely prevent an undesired transfer. Furthermore, a method for producing such an adhesive structure is to be provided.

These objects are achieved by a silicone-gel-coated, adhesive layer structure which comprises a first layer consisting of a porous backing material, a crosslinked or uncrosslinked intermediate layer on only one side of the porous backing material and a layer made of a crosslinked, adhesive silicone gel on the intermediate layer. Moreover, these objects are achieved by a method for producing the silicone-coated, adhesive layer structure in which an intermediate layer material is applied, partially or completely covering it, to a porous backing material, the intermediate layer material is optionally crosslinked, a silicone gel is applied to the crosslinked or uncrosslinked intermediate layer material and the silicone gel is then crosslinked. The intermediate layer acts as a barrier layer for the silicone gel and prevents the silicone gel from permeating or bleeding through the porous backing material. In addition, the intermediate layer brings about a good bonding of the silicone gel to the layer structure.

The layer structure according to the invention is preferably a medical product, particularly preferably a roll plaster, in particular a roll plaster for securing medical instruments to the skin of a person or animal.

The adhesive layer structure, as well as the production and use thereof is described more precisely in the following with reference to their various embodiments.

Silicone-Coated, Adhesive Layer Structure

According to the invention, the adhesive layer structure comprises a first layer consisting of a porous backing material, a crosslinked or uncrosslinked intermediate layer on one side of the porous backing material and a layer made of a crosslinked, adhesive silicone gel on the intermediate layer.

The Porous Backing Material

In order to facilitate a best possible wearing comfort, according to the invention the backing material is manufactured from a soft and elastic material.

The backing material can be produced from natural material or plastic. In particular, viscose, rayon, cellulose, polyethylene, polypropylene, polyamide, polyester, polyacetate, polyurethane or a mixture thereof comes into consideration here. The backing material is preferably manufactured from polyester.

In order to guarantee a best possible transport of oxygen and moisture through the adhesive layer structure to the skin of the person or animal, the backing material according to the invention is porous.

According to an embodiment, the above-named materials are present in the form of a non-woven material, fabric, knitted fabric, foam material or a film. The above-named materials are preferably present in the form of a non-woven material.

Intermediate Layer Material

In order to prevent the adhesive silicone gel from permeating or bleeding through the porous backing, there is an intermediate layer between the porous backing and the silicone gel layer. The intermediate layer material is preferably present on only the side of the porous backing material facing the silicone gel; the other side of the porous backing material is free from intermediate layer material. The intermediate layer can be present crosslinked or uncross linked.

According to an embodiment, the porous backing material is completely covered with the crosslinked or uncrosslinked intermediate layer.

According to a further embodiment, the porous backing material is partially covered with the crosslinked or uncrosslinked intermediate layer. By partially, within the framework of this invention, is meant any uniformly distributed coverage of the porous backing material with the intermediate layer material which is not complete.

The side of the porous backing material covered with the intermediate layer material is covered with the intermediate layer material in the range of from 30 to 100%, preferably 40 to 100%, more preferably 50 to 100%, still more preferably 60 to 100%, most preferably 70 to 100%, in particular 80 to 100%.

According to the invention, the crosslinked or uncrosslinked, intermediate layer is present on the porous backing material in a quantity of from 10 to 500 $g/m^2$, preferably 10 to 400 $g/m^2$, more preferably 10 to 300 $g/m^2$, still more preferably 10 to 200 $g/m^2$, particularly preferably 10 to 100 $g/m^2$, most preferably 33 $g/m^2$.

The presence of the intermediate layer according to the invention has the result that the adhesive silicone gel can be prevented from permeating or bleeding through even when the intermediate layer material only partially covers the porous backing material, as the flowability of the silicone gel comes to a halt due to crosslinking before the silicone gel can flow in the uncovered areas of the porous backing material to the porous backing material.

According to an embodiment, the intermediate layer material comprises an acrylic acid copolymer. According to a preferred embodiment, the intermediate layer consists of the acrylic acid copolymer. According to a more preferred embodiment, the acrylic acid copolymer is produced from monomers of the group consisting of acrylic acid, butyl acrylate, 2-ethylhexyl acrylate, 2-hydroxyethyl acrylate, dioctyl acrylate, methyl acrylate, ethyl acrylate, tert-butyl acrylate and mixtures thereof.

Silicone Gel

The adhesive layer structure furthermore comprises an adhesive silicone gel applied to the crosslinked or uncrosslinked intermediate layer. The intermediate layer material and the adhesive silicone gel are preferably present on only one side of the porous backing material; the other side of the porous backing material is free from intermediate layer material and adhesive silicone gel.

Silicone gel, within the framework of this invention, means a silicone material composed of at least one silicone base material and a catalyst. Silicone base material, within the framework of this invention, means a silicone material in the uncrosslinked or slightly crosslinked state, which yields a silicone gel as a mixture with at least one catalyst. The silicone base material can be present in monomeric or polymeric form. The catalyst serves to crosslink the silicone base material.

Silicone base materials according to the invention are, for example, vinyl-functional polydimethylsiloxanes or hydrogen-functional siloxanes, for example hydromethyl siloxanes. The catalyst is selected from usual catalysts known to a person skilled in the art which are used to crosslink silicone gels. The catalyst preferably comprises a noble metal. The catalyst particularly preferably comprises platinum, palladium or nickel, in particular platinum. In particular, the so-called Karstedt's catalyst is used. Commercially available silicone systems which comprise a silicone base material and a catalyst are preferably used, wherein the silicone base material and the catalyst are present spatially separate from each other, with the result that no undesired crosslinking begins. The components are not mixed with each other until shortly before application of the silicone gel to the intermediate layer. Silicone systems used according to the invention are, for example, the MED 6342 silicone system from NuSil Technology LLC or the Silpuran 2110 A/B silicone system from Wacker Chemie AG.

According to an embodiment, the adhesive silicone gel is present on the crosslinked or uncrosslinked intermediate layer in a quantity of from 10 to 500 $g/m^2$, preferably 50 to 200 $g/m^2$, most preferably 80 to 120 $g/m^2$, in particular 100 $g/m^2$.

The silicone-coated, adhesive layer structure according to the invention is preferably a medical product, such as for example a roll plaster or a tape.

The silicone-coated, adhesive layer structure according to the invention is particularly preferably used for securing to the skin of a person or animal. It can serve, for example, to secure medical instruments to the skin of the person or animal.

Method

The invention furthermore relates to a method for producing the adhesive layer structure according to the invention.

According to the invention, an intermediate layer material is first applied to a porous backing material. The intermediate layer material is preferably applied to only one side of the porous backing material, wherein the other side of the porous backing material is free from intermediate layer material.

According to an embodiment, the intermediate layer material is applied, completely covering it, to the porous backing material. According to another embodiment, the intermediate layer material is applied, partially covering it, to the porous backing material. Optionally, the intermediate layer material is crosslinked after application to the porous backing material. Then a silicone gel is applied to the crosslinked or uncrosslinked intermediate layer material. The silicone gel is preferably applied only to the intermediate layer material and not to the side of the porous backing material free from intermediate layer material, with the result that one side of the porous backing material is free from intermediate layer material and silicone gel. Finally, the silicone gel is crosslinked.

Application of the Intermediate Layer

According to an embodiment, the intermediate layer material is applied in an uncrosslinked or crosslinked form directly, completely or partially covering it, to the porous backing material, and then optionally (further) crosslinked.

According to a preferred embodiment, the intermediate layer material is not applied to the porous backing immediately, but to a substrate material first, for example siliconized release liner. The intermediate layer material is then applied, completely or partially covering it, to the porous backing from this substrate material by means of transfer coating, for example laminating.

Optionally, the intermediate layer material is crosslinked after application to the porous backing material and before the silicone gel is applied to the intermediate layer.

According to an embodiment, the intermediate layer material is crosslinked thermally. According to the invention this comprises any crosslinking in which the energy needed is provided by heat (thermally). Thermal crosslinking within the framework of this invention therefore also comprises a crosslinking at ambient temperature, for example room temperature. The crosslinking duration is reciprocally dependent on the heat energy supplied (thus the temperature). The higher the crosslinking temperature, the shorter the crosslinking duration, and vice versa.

According to another embodiment, the intermediate layer material is crosslinked by UV radiation. According to the invention this comprises any crosslinking in which the energy needed is provided by UV radiation.

Hybrids of thermal and UV crosslinking likewise fall within the framework of this invention. Thus, for example, it is possible for the crosslinking to be effected at an increased temperature and for the intermediate layer additionally to be irradiated with UV radiation.

The intermediate layer material is preferably crosslinked through the porous backing material by means of UV radiation. The UV radiation is thus applied not directly to the intermediate layer material, but to the porous backing material. In this way, a particularly good bonding between porous backing material and the intermediate layer is guaranteed.

In the case of a transfer coating, the intermediate layer material is present preferably dissolved in a solvent, preferably water, benzine or acetone, before application to the substrate material. In this case, the intermediate layer material dissolved in the solvent is applied to the substrate material and the solvent is then removed, preferably evaporated. This can be effected, for example, in a circulating air flotation dryer at 180° C.

According to a preferred embodiment, the intermediate layer material present on the substrate material is crosslinked before being applied, completely or partially covering it, to the porous backing material by means of transfer coating. The crosslinking is effected thermally or by means of UV radiation. Hybrids of thermal and UV crosslinking likewise fall within the framework of this invention.

The intermediate layer material is generally applied to the porous backing material in a quantity of from 10 to 500 g/m$^2$, preferably 10 to 400 g/m$^2$, more preferably 10 to 300 g/m$^2$, still more preferably 10 to 200 g/m$^2$, particularly preferably 10 to 100 g/m$^2$, most preferably 33 g/m$^2$. Here, 30 to 100%, preferably 40 to 100%, more preferably 50 to 100%, still more preferably 60 to 100%, most preferably 70 to 100%, in particular 80 to 100%, of one side of the porous backing material is covered with the intermediate layer material.

Application of the Silicone Gel Layer to the Crosslinked or Uncrosslinked Intermediate Layer After the intermediate layer has been applied to the porous backing material and optionally crosslinked, an adhesive silicone gel is applied to the crosslinked or uncrosslinked intermediate layer material. The silicone gel can be applied, for example, with a film applicator. The silicone gel is preferably applied only to the intermediate layer material and not to the side of the porous backing material free from intermediate layer material, with the result that one side of the porous backing material is free from intermediate layer material and silicone gel.

The adhesive silicone gel is applied to the crosslinked or uncrosslinked intermediate layer in a quantity of from 10 to 500 g/m$^2$, preferably 50 to 200 g/m$^2$, most preferably 80 to 120 g/m$^2$, in particular 100 g/m$^2$.

The silicone gel is crosslinked after application. According to a preferred embodiment, the silicone gel is crosslinked thermally. This can occur, for example, by the layer structure being guided through a drying tunnel. A person skilled in the art will set the precise crosslinking temperature and duration as a function of the respective silicone gel.

The silicone gel is preferably designed such that the layer structure adheres well to the skin of a patient, can be removed from the skin easily and with minimal detachment of skin cells and hair, displays an optimal and constant adhesive force over the entire duration of the application and at the same time is gentle and pleasant for the skin. Furthermore, the technical parameters are chosen such that the layer made of silicone gel has a very good anchoring to the intermediate layer lying underneath, with the result that a transfer onto the skin can be reduced and ideally ruled out altogether.

The silicone gel is formed by mixing the silicone base material with the catalyst preferably only shortly before application to the intermediate layer, it is then applied to the intermediate layer in the desired quantity and subsequently crosslinked, preferably thermally. The mixing ratio of the components depends on the respective silicone base material and catalyst and can be set individually depending on the use.

EMBODIMENT EXAMPLES

Example 1

An elastic, porous polyester non-woven material (Sontara® from DuPont) is selected as backing material. The backing material is coated with a pressure-sensitive adhesive made of acrylic acid copolymer (Duro Tak 1154 from Henkel) by means of transfer coating. For the transfer coating, a siliconized release liner (G-liner silicone from Mondi) is first coated with 33 g/m$^2$ acrylate adhesive with a film applicator. The coated release liner is dried in a circulating air flotation dryer at 180° C. and then irradiated with UV radiation of an intensity of 3.3 mJ/cm$^2$ and thus crosslinked. The adhesive side is irradiated directly here. Then the acrylate compound is applied to the polyester non-woven material by means of transfer coating from the release liner. The thus-formed coated polyester non-woven material is again conveyed through a radiation chamber and irradiated with UV light of an intensity of 265 mJ/cm$^2$. Here, the backing side is irradiated and thus the adhesive is crosslinked through the backing. Then the coated non-woven material is coated with a two-component silicone gel (Silpuran 2110 A/B from Wacker Chemie AG). Here, the silicone gel is applied to the already present, crosslinked acrylate layer. The silicone gel is applied in an application weight of 100 g/m$^2$ with a film applicator. The coated non-woven material is guided through a drying tunnel at 150° C. at 5 m/min and the silicone gel is thereby crosslinked. The coated non-woven material is finally covered with a siliconized release liner.

Example 2

To produce the adhesive layer structure, an elastic, porous polyester non-woven material (Sontara® from DuPont) is selected as backing material. The backing material is coated directly with a pressure-sensitive adhesive made of acrylic acid copolymer (acResin A 260 UV from BASF AG). The adhesive is a hot-melt adhesive. This is first liquefied at a temperature of 130° C. in a drum melter and applied directly to the polyester non-woven material in an application quantity of 33 g/m$^2$ with the aid of a slot die. A subsequent drying was dispensed with. The coated non-woven material is irradiated with UV light as described in Example 1, in order to crosslink the adhesive. Then the coated non-woven material is coated with a two-component silicone gel (Silpuran 2110 A/B from Wacker Chemie AG). Here, the silicone gel is applied to the already present acrylate layer. The silicone gel is applied in an application weight of 100 g/m$^2$ with a film applicator. The coated non-woven material is guided through a drying tunnel at 150° C. at 5 m/min and the silicone gel is thereby crosslinked. The coated non-woven material is finally covered with a siliconized release liner.

The invention claimed is:

1. Silicone-gel-coated, adhesive layer structure, comprising:
   a) a first layer having a porous backing material,
   b) on one side of the porous backing material, an intermediate layer which comprises acrylic acid copolymer crosslinked by UV radiation and,
   c) applied on the intermediate layer, a layer made of a crosslinked, adhesive silicone gel, wherein the acrylic acid copolymer is crosslinked by UV radiation through the porous backing material of the first layer, wherein the intermediate layer defines an enhanced bond between the porous backing material and the intermediate layer.

2. Adhesive layer structure according to claim 1, wherein the intermediate layer and the adhesive silicone gel are present only on one side of the porous backing material.

3. Adhesive layer structure according to claim 1 wherein the porous backing material is selected from the group consisting of non-woven materials, fabrics, knitted fabrics, foam materials and films.

4. Adhesive layer structure according to claim 1 wherein the porous backing material is selected from the group consisting of natural material, viscose, rayon, cellulose, polyethylene, polypropylene, polyamide, polyester, polyacetate, and polyurethane or a mixture thereof.

5. Adhesive layer structure according to claim 1 wherein the crosslinked intermediate layer is present on the porous backing material in a quantity of from 10 to 500 $g/m^2$.

6. A medical product having a silicone-gel-coated, adhesive layer structure according to claim 1 and adapted for securing a medical device to the skin of a person or an animal.

7. Adhesive layer structure according to claim 1, wherein the crosslinked intermediate layer is present on the porous backing material in a quantity of from 10 to 300 $g/m^2$.

8. Adhesive layer structure according to claim 1, wherein the crosslinked intermediate layer is present on the porous backing material in a quantity of from 10 to 200 $g/m^2$.

9. Adhesive layer structure according to claim 1, wherein the crosslinked intermediate layer is present on the porous backing material in a quantity of from 10 to 100 g/m2.

10. Adhesive layer structure according to claim 1, wherein the crosslinked intermediate layer is present on the porous backing material in a quantity of 33 $g/m^2$.

11. Adhesive layer structure according to claim 1, wherein the acrylic acid copolymer is produced from monomers of the group consisting of acrylic acid, butyl acrylate, 2-ethylhexyl acrylate, 2-hydroxyethyl acrylate, dioctyl acrylate, methyl acrylate, ethyl acrylate, and tert-butyl acrylate, and mixtures thereof.

12. Adhesive layer structure according to claim 1, wherein one side of the porous backing material is 30 to 100 percent covered with the intermediate layer material.

13. Adhesive layer structure according to claim 1, wherein one side of the porous backing material is 40 to 100% covered with the intermediate layer material.

14. Adhesive layer structure according to claim 1, wherein one side of the porous backing material is 50 to 100% covered with the intermediate layer material.

15. Adhesive layer structure according to claim 1, wherein one side of the porous backing material is 60 to 100% covered with the intermediate layer material.

16. Adhesive layer structure according to claim 1, wherein one side of the porous backing material is 70 to 100% covered with the intermediate layer material.

17. Adhesive layer structure according to claim 1, wherein one side of the porous backing material is 80 to 100% covered with the intermediate layer material.

18. Adhesive layer structure according to claim 1, wherein the crosslinked, adhesive silicone gel layer is present on the crosslinked intermediate layer in a quantity of from 10 to 500 $g/m^2$.

19. Adhesive layer structure according to claim 1, wherein the crosslinked, adhesive silicone gel layer is present on the crosslinked intermediate layer in a quantity of from 50 to 200 $g/m^2$.

20. Adhesive layer structure according to claim 1, wherein the crosslinked, adhesive silicone gel layer is present on the crosslinked intermediate layer in a quantity of from 80 to 120 $g/m^2$.

21. Adhesive layer structure according to claim 1, wherein the crosslinked, adhesive silicone gel layer is present on the crosslinked intermediate layer in a quantity of 100 $g/m^2$.

22. Adhesive layer structure according to claim 1, wherein the adhesive layer structure is a medical product.

23. A multi-layer adhesive medical bandage, comprising:
   (a) a porous, air and moisture-transmissive elastic backing material;
   (b) an intermediate layer positioned on a first side of the elastic backing material;
   (c) a skin-side adhesive silicone gel positioned on a side of the intermediate layer remote from the elastic backing material;
   (d) the skin-side adhesive silicone gel comprising a UV crosslinked adhesive silicone gel wherein the UV crosslinking occurred through the elastic backing material and intermediate layer; and
   (e) the UV crosslinked adhesive silicone gel defining an enhanced bond with the elastic backing material and the intermediate layer.

* * * * *